US009139500B2

(12) United States Patent
Trippeer et al.

(10) Patent No.: US 9,139,500 B2
(45) Date of Patent: Sep. 22, 2015

(54) SELECTIVE DEHYDROHALOGENATION OF TERTIARY HALOGENATED HYDROCARBONS AND REMOVAL OF TERTIARY HALOGENATED HYDROCARBON IMPURITIES FROM A HALOGENATED HYDROCARBON PRODUCT

(71) Applicant: Dow AgroSciences LLC, Indianapolis, IN (US)

(72) Inventors: Michael Lee Trippeer, Midland, MI (US); Timothy C. Frank, Midland, MI (US); Patrick H. Au-Yeung, Midland, MI (US); Jason L. Bronkema, Midland, MI (US); Robin K. Johnston, Missouri City, TX (US); Mukund R. Patel, Midland, MI (US); Bruce S. Holden, Midland, MI (US); Terrence McCabe, Midland, MI (US); Daniel A. Hickman, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 214 days.

(21) Appl. No.: 13/835,951

(22) Filed: Mar. 15, 2013

(65) Prior Publication Data
US 2013/0206578 A1 Aug. 15, 2013

Related U.S. Application Data

(62) Division of application No. 12/803,345, filed on Jun. 24, 2010, now Pat. No. 8,449,729.

(60) Provisional application No. 61/269,594, filed on Jun. 26, 2009.

(51) Int. Cl.
*B01D 3/00* (2006.01)
*C07C 17/395* (2006.01)
(Continued)

(52) U.S. Cl.
CPC ............... *C07C 17/395* (2013.01); *B01D 3/00* (2013.01); *B01D 3/34* (2013.01); *C07C 17/383* (2013.01); *C07B 2200/09* (2013.01)

(58) Field of Classification Search
CPC .................................. B01D 3/00; B01D 3/34
USPC .............. 23/22, 28, 99; 570/216, 238; 203/29
See application file for complete search history.

(56) References Cited

U.S. PATENT DOCUMENTS 2,322,258 A    6/1943  Strosacker et al.
2,389,230 A *  11/1945  Blumer ......................... 570/242
(Continued)

FOREIGN PATENT DOCUMENTS

JP    42008849    4/1967
JP    5233605 A    3/1977
(Continued)

OTHER PUBLICATIONS

"Dimerization of Proipylene to 4-methyl-1-pentene with catalysts from potassium", John B. Wilkes, Apr. 1967, World Petroleum Congress.
(Continued)

*Primary Examiner* — Robert A Hopkins
(74) *Attorney, Agent, or Firm* — Carl D. Corvin; Maschoff Brennan

(57) ABSTRACT

A process for converting a tertiary halogenated hydrocarbons in a tertiary halogenated hydrocarbon-containing stream to a corresponding unhalogenated or less-halogenated unsaturated hydrocarbon product with the release of hydrogen halide involves contacting the tertiary halogenated hydrocarbon with a sorbent-type dehydrohalogenation catalyst in a reaction zone and optionally passing a stripping gas through the reaction zone to remove vapor phase reaction products from the reaction zone. A process for removing a tertiary chlorinated hydrocarbon impurity from 1,3-dichloro-1-propene involves contacting a mixture containing the 1,3-dichloro-1-propene and the tertiary chlorinated hydrocarbon impurity with a dehydrochlorination catalyst effective to catalyze a conversion of the tertiary chlorinated hydrocarbon impurity to a corresponding unchlorinated or less-chlorinated unsaturated hydrocarbon and hydrogen chloride and distilling the 1,3-dichloro-1-propene to produce a purified cis-1,3-dichloro-1-propene fraction and a purified trans-1,3-dichloro-1-propene fraction.

11 Claims, 6 Drawing Sheets

(51) Int. Cl.
*B01D 3/34* (2006.01)
*C07C 17/383* (2006.01)

(56) References Cited

U.S. PATENT DOCUMENTS

| | | | |
|---|---|---|---|
| 2,490,973 | A | 12/1949 | Leonard et al. |
| 2,899,473 | A | 8/1959 | Leprince et al. |
| 2,920,122 | A | 1/1960 | Milton et al. |
| 3,240,834 | A | 3/1966 | Kruse et al. |
| 3,247,277 | A | 4/1966 | Kruse et al. |
| 3,257,472 | A | 6/1966 | Kruse |
| 3,274,273 | A | 9/1966 | Lester at al. |
| 3,277,204 | A | 10/1966 | Ferstandig et al. |
| 3,277,205 | A | 10/1966 | Hughes |
| 3,329,730 | A | 7/1967 | Vives |
| 3,363,022 | A | 1/1968 | Harrison |
| 3,372,207 | A | 3/1968 | Hutson, Jr. |
| 3,401,211 | A | 9/1968 | Hutson, Jr. |
| 3,445,538 | A | 5/1969 | Kahn |
| 3,523,982 | A | 8/1970 | Vives |
| 3,676,518 | A | 7/1972 | Hoppstock et al. |
| 3,870,762 | A | 3/1975 | Stacey et al. |
| 3,908,009 | A | 9/1975 | Polemenakos et al. |
| 4,319,062 | A | 3/1982 | Boozalis et al. |
| 4,384,159 | A | 5/1983 | Diesen |
| 4,827,057 | A | 5/1989 | Kasbauer et al. |
| 5,107,061 | A | 4/1992 | Ou et al. |
| 5,763,711 | A | 6/1998 | Ito |
| 6,881,872 | B2 | 4/2005 | Matsumoto et al. |
| 2003/0164284 | A1 | 9/2003 | Matsumoto et al. |

FOREIGN PATENT DOCUMENTS

| | | |
|---|---|---|
| JP | 2002-105007 A1 | 2/2003 |
| WO | WO 97/03035 | 1/1997 |

OTHER PUBLICATIONS

Patent Cooperation Treaty International Search Report. PCT Patent Application No. PCT/US2010/001841, Sep. 1, 2010.

Patent Cooperation Treaty Written Opinion of the International Searching Authority. PCT Patent Application No. PCT/US2010/001841. Sep. 1, 2010.

Ballinger, Todd H., Smith, R. Scott, Colson, Steven D., and Yates, John T. Thermal Decomposition of 1,1,1-Trichloroethane and 1,1-Dichloroethene over High Surface Area Alumina. Journal of Physical Chemistry, 1992, vol. 96(3), pp. 1417-1423.

Kanyi, Charles W.; Doetschman, David C.; Yang, Szu-Wei; Schulte, Jurgen; and Jones, Barry R. Room temperature reactions of alkyl halides in zeolite NaX: Dehalogenation versus dehydrohalogenation. Microporous and Mesororous Materials, 2008, vol. 108, pp. 103-111.

* cited by examiner

SELECTIVE DEHYDROHALOGENATION OF TERTIARY HALOGENATED HYDROCARBONS AND REMOVAL OF TERTIARY HALOGENATED HYDROCARBON IMPURITIES FROM A HALOGENATED HYDROCARBON PRODUCT

CROSS REFERENCE TO RELATED APPLICATION

The present application is a divisional of U.S. patent application Ser. No. 12/803,345 filed on Jun. 24, 2012, now U.S. Pat. No. 8,449,729, which claims the benefit of U.S. Provisional Patent Application No. 61/269,594 filed Jun. 26, 2009, which is incorporated herein by reference in its entirety.

BACKGROUND

The present invention relates to the field of halogenated hydrocarbons and the manufacture and purification of same, and more particularly, but not exclusively, relates to processes for dehydrohalogenating tertiary halogenated hydrocarbons, which processes have utility, for example, in the removal of a tertiary halogenated hydrocarbon impurity from a manufacturing process stream.

1,3-Dichloro-1-propene is a useful commercial compound in the medical and agricultural fields. Dow AgroSciences, Inc., (Zionsville, Ind.) produces a mix of cis and trans isomers of 1,3-dichloro-1-propene under the trademark Telone II® for use as a soil fumigant to control nematodes.

1,3-Dichloro-1-propene is a by-product, or co-product, of the chemical reactions employed to produce allyl chloride, and thus commercial 1,3-dichloro-1-propene products can be made by isolating a byproduct fraction from an allyl chloride production plant that includes 1,3-dichloro-1-propene (referred to herein as a "Telone crude" fraction), and then subjecting the Telone crude to a distillation process to separate and recover 1,3-dichloro-1-propene from the other by-products and impurities that are produced in the allyl chloride manufacturing process and that separate into the Telone crude fraction. While distillation processing is suitable to achieve desired purity levels with respect to many of the by-products and impurities in the Telone crude, one particular tertiary chlorinated alkane species, 2-chloro-2-methylpentane, cannot effectively be separated from 1,3-dichloro-1-propene by distillation to meet desired purity levels.

There exists a need for processes effective to remove a 2-chloro-2-methylpentane impurity from 1,3-dichloro-1-propene and, more generally, a need to remove tertiary halogenated hydrocarbon impurities from a hydrocarbon product. The present application addresses these needs and provides additional benefits.

SUMMARY

In one aspect, the present application provides methods, systems and devices for dehydrohalogenating one or more tertiary halogenated hydrocarbons.

In another aspect of the present application, there are provided methods, systems and devices for removing one or more tertiary halogenated hydrocarbon impurity, such as, for example, a tertiary chlorinated alkane or alkene impurity, from a mixture of halogenated hydrocarbon compounds. In one embodiment, the tertiary halogenated hydrocarbon is removed from a manufacturing process stream or a waste stream. The method includes selectively dehydrohalogenating the one or more tertiary halogenated hydrocarbons and removing reaction products in a stripping gas and/or by distillation. Such methods, and corresponding systems and devices, are useful, for example, in industrial processes for purifying one or more halogenated target compounds. In one embodiment, there is provided a method for removing a 2-choro-2-methylpentane impurity from 1,3-dichloro-1-propene.

Further embodiments, forms, features, advantages, aspects, and benefits shall become apparent from the following description and drawings.

DETAILED DESCRIPTION

Figure 1:
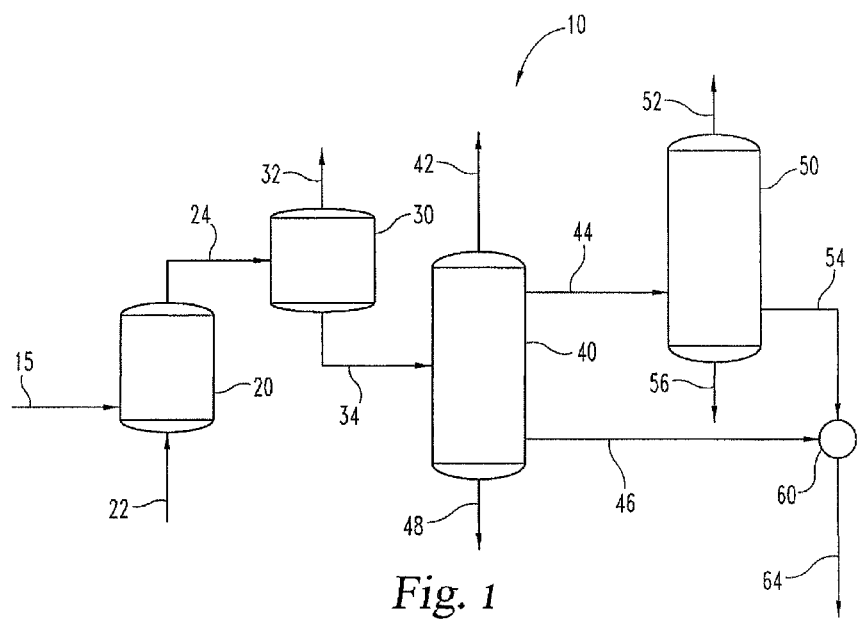
FIG. 1 is a schematic view of a 1,3-dichloro-1-propene purification system in accordance with one embodiment of the present application.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In one aspect, the present application relates to the discovery of certain techniques for selectively dehydrohalogenating tertiary halogenated hydrocarbons to convert the tertiary halogenated hydrocarbon into a corresponding lesser-halogenated or non-halogenated alkene accompanied by the release of hydrogen halide (i.e., hydrogen chloride, hydrogen fluoride and/or hydrogen bromide). As used herein, the term "tertiary halogenated hydrocarbon" refers to a hydrocarbon in which a carbon bound to three carbon neighbors (i.e., a tertiary carbon) is also bound to a halogen, and which includes a beta hydrogen. In one embodiment, the tertiary halogenated hydrocarbon is a tertiary chlorinated alkane or alkene. In another embodiment, the tertiary halogenated hydrocarbon is a tertiary halogenated alkane, such as, for example, a tertiary chlorinated alkane. In yet another embodiment, the tertiary halogenated hydrocarbon comprises 2-chloro-2-methylpentane. Because the dehydrohalogenation catalysts described herein are effective to selectively dehydrohalogenate tertiary halogenated hydrocarbons in a mixture without altering other halogenated hydrocarbons in the mixture, catalyzed dehydrohalogenation reactions described herein can be employed in processes for purifying halogenated hydrocarbon products. Thus, another aspect of the application relates to the dehydrohalogenation of one or more tertiary halogenated hydrocarbons as an additional treatment phase of an industrial distillation process for enhancing the purity levels of one or more target compounds.

In certain aspects of the present application, attention is given to the dehydrochlorination of tertiary chlorinated hydrocarbons and the removal of tertiary chlorinated hydrocarbons from a flow stream mixture that includes one or more tertiary chlorinated hydrocarbon and other halogenated hydrocarbons. It is to be understood, however, that the present application also contemplates application of the principles described herein to tertiary halogenated hydrocarbons that comprise halogens other than chlorine. In addition, while one or more embodiments described herein involve the dehydrochlorination of tertiary chlorinated alkanes, the present application also contemplates application of the principles described herein to tertiary halogenated alkenes, such as, for example, 4-chloro-4-methyl-1-pentene, or other tertiary halogenated hydrocarbons that include a beta hydrogen. Therefore, for purposes of the present specification, embodiments relating to tertiary chlorinated alkanes are also intended to apply to tertiary halogenated hydrocarbons, whether alkanes, alkenes, or other hydrocarbons having a halogen bonded to a tertiary carbon and comprising a beta hydrogen, as if each of these alternative embodiments were expressly named.

In a process for converting tertiary halogenated hydrocarbons to corresponding less-halogenated or non-halogenated alkenes and hydrogen halide according to the present application, the tertiary halogenated hydrocarbons are contacted with a sorbent-type dehydrohalogenation catalyst. It has been discovered that commercially effective conversion rates can be achieved by effecting the catalyzed reaction in the liquid phase at a temperature less than the dew point of the mixture containing the tertiary halogenated hydrocarbon reactant or in the vapor phase at a temperature above the dew point of the mixture. In one embodiment, the catalyzed reaction is effected at a temperature of less than about 135° C. Conducting the reaction in the liquid phase can be effective in some embodiments to save the energy that would otherwise be necessary to vaporize the process stream; however, in other embodiments, such as, for example, where a process stream is already in the vapor phase, the reaction can be performed in the vapor phase without input of significant amounts of energy.

The dehydrohalogenation catalyst utilized in the methods and systems described herein is a sorbent-type dehydrohalogenation catalyst. As used herein, the terms "dehydrohalogenation catalyst," "dehydrochlorination catalyst," "sorbent-type dehydroahlogenation catalyst," "sorbent-type dehydrochlorination catalyst" and "sorbent-type catalyst" are used interchangeably to refer to a traditional adsorbent that includes silicon oxide and/or aluminum oxide, such as, for example, activated alumina (aluminum oxides), sintered alumina (aluminum oxide), activated clay (silicon and aluminum oxides), fumed silica or silica gel (silicon oxide), and magnesium silicate (a silicon oxide). In one embodiment, the sorbent-type catalyst is in its natural form, i.e., without having been pretreated with any special doping or metals. Representative commercially available activated clay catalysts that can be used in the processes described herein include, for example, mordenite, which is commercially available from a number of zeolite suppliers such as Sud-Chemie Inc. (Louisville, Ky.) and Tonsil™, which is commercially available from Sud-Chemie Inc. (Louisville, Ky.). In one embodiment the activated alumina catalyst comprises a neutral grade activated alumina or an acidic grade activated alumina. A representative commercially available activated alumina catalyst that can be used in the processes described herein is F-200 activated alumina, which is commercially available from BASF Catalysts LLC (Iselin, N.J.). In another embodiment, the catalyst comprises an acidic or neutral aluminum oxide catalyst that has been sintered to reduce the surface area and acidity. Materials of this type are commercially available from BASF Catalysts LLC (Iselin, N.J.). In other embodiments, the catalyst is a silica gel or a zeolite.

The selective catalyzed dehydrohalogenation reaction can be conducted in a reactor defining a reaction chamber in which the catalyst is contained. The tertiary halogenated hydrocarbon, or a mixture containing same, is passed through the reaction chamber in contact with the catalyst. In one embodiment, an inert stripping gas is also passed through the reaction chamber. The stripping inert gas operates to remove the hydrogen halide reaction product from the reaction chamber, thereby helping to drive the equilibrium of the reaction toward the product side. Depending upon the reaction temperature, the addition of the inert gas also increases the percentage of the feed that is in the vapor phase in the reactor. The stripping gas can comprise any inert gas. As used herein, the term "inert gas" refers to any compound or element that is a stable gas at a temperature and under conditions present in the dehydrohalogenation reactor, such as nitrogen, helium, argon or light hydrocarbon.

The catalyst can have a variety of physical forms suitable for achieving an acceptable level of contact with the reactant(s), many examples of which are well known to persons skilled in the art. Preferred forms are those that provide high surface area for contact with the reactant(s). For example, and without limitation, the catalyst can be provided in a particulate form in a packed bed or a fluidized bed or in a structured form, such as, for example, structured packing or baffles as described further hereinbelow.

Reaction conditions in which the reactants are in the liquid phase or in the gas phase when contacted with the catalyst are suitably employed, but a gas phase reaction is presently preferred. In one embodiment in which the catalyzed reaction is conducted in the liquid phase, prescribed reaction conditions, as conducted with a packed bed, a fluidized bed or a structured form, include maximum catalyst temperature of about 125° C., a pressure of from about 0.5 to about 50 psia, stripping gas flow rates from 0 to about 4000 hr−1 gas hourly space velocity (GHSV) and liquid feed flow rates from 0 to about 4000 weight hourly space velocity (WHSV). In another embodiment, in which the catalyzed reaction is conducted in the gas phase, prescribed reaction conditions, as conducted with a packed bed, a fluidized bed or a structured form, include maximum catalyst temperature of about 200° C., a pressure of from about 0.5 to about 100 psia, stripping gas flow rates from 0 to about 4000 hr−1 gas hourly space velocity (GHSV) and gaseous feed flow rates from 0 to about 4000 hr−1 gas hourly space velocity (GHSV).

In one embodiment, the reaction is carried out at a temperature of from about 20 to about 150° C. In another embodiment, the reaction is carried out at a temperature of from about 50 to about 125° C. In yet another embodiment, the reaction is carried out at a temperature of from about 60 to about 115° C. in still another embodiment, the reaction is carried out at a temperature of from about 90 to about 105° C. In still yet another embodiment, the reaction is carried out at a temperature of from about 90 to about 125° C. In yet another embodiment, the reaction is carried out at a temperature of from about 90 to about 115° C.

In one embodiment, the reaction is carried out at a pressure of from about 0.5 to about 50 psia. In another embodiment, the reaction is carried out at a pressure of from about 5 to about 30 psia. In yet another embodiment, the reaction is carried out at a pressure of from about 10 to about 25 psia. In still another embodiment, the reaction is carried out at a pressure of from about 14 to about 20 psia. In still yet another embodiment, the reaction is carried out at atmospheric pressure.

The catalyzed dehydrohalogenation reactions discussed above can be advantageously employed to remove a tertiary halogenated alkane and/or tertiary chlorinated alkene impurity from a target compound or mixture, such as, for example, from a halogenated hydrocarbon compound or a mixture including one or more halogenated hydrocarbon compounds. This is commercially useful, for example, to purify a target compound or mixture in a manufacturing process stream that includes one or more tertiary halogenated alkane and/or tertiary halogenated alkene impurities or to recover hydrogen halide and hydrocarbons from a waste stream that includes one or more tertiary halogenated alkanes and/or tertiary chlorinated alkenes. The methods and systems described herein can also be employed as a production technique to produce specific hydrocarbon compounds from tertiary halogenated hydrocarbons.

With regard to the removal of a tertiary halogenated alkane and/or tertiary halogenated alkene impurity from a compound or mixture, a method includes dehydrohalogenating one or more tertiary halogenated alkane and/or tertiary halogenated alkene using a dehydrohalogenation catalyst as described above, together with one or more distillation treatments. One embodiment of the present application is a method for separating and recovering 1,3-dichloro-1-propene from a flow stream that also includes one or more tertiary chlorinated alkane and/or tertiary chlorinated alkene impurities. The method includes contacting the flow stream with a suitable sorbent-type catalyst for conversion of the one or more tertiary chlorinated alkane and/or tertiary chlorinated alkene impurity in the flow stream into one or more corresponding alkenes, i.e., corresponding unchlorinated or less-chlorinated unsaturated hydrocarbons, and hydrogen chloride. The corresponding alkenes produced in the reactor are readily distillable from 1,3-dichloro-1-propene, and thus conversion of the tertiary chlorinated alkane and/or tertiary chlorinated alkene impurities to corresponding unchlorinated or less-chlorinated alkenes, followed by distillation can effectively remove the tertiary chlorinated alkane and/or tertiary chlorinated alkene impurities from 1,3-dichloro-1-propene. In one embodiment, the reaction products, along with any other impurities that may be present, are distilled in a two column configuration, a first column effective to separate and purify the trans isomer of 1,3-dichloro-1-propene, and the second column effective to separate the cis isomer of 1,3-dichloro-1-propene from impurities. This process allows for the production of a more highly purified 1,3-dichloro-1-propene product compared to processes known and used in the prior art, and assists in meeting heightened purity standards.

Referring now to FIG. 1, there is shown one illustrative process scheme for purifying a 1,3-dichloro-1-propene product. Feed stream 15 of system 10 includes 1,3-dichloro-1-propene and at least one tertiary chlorinated alkane and/or tertiary chlorinated alkene impurity. In one embodiment, feed stream 15 comprises a mixed cis- and trans-1,3-dichloro-1-propene product that includes a tertiary chlorinated alkane and/or tertiary chlorinated alkene impurity, such as the commercially available Telone II® pesticide product, which is a commercially available mixture of cis- and trans-1,3-dichloro-1-propene that includes some residual tertiary chlorinated alkane and/or tertiary chlorinated alkene impurities, such as, for example, the tertiary chlorinated alkane 2-chloro-2-methylepentane, the tertiary chlorinated alkane 2-chloro-2,3-dimethylbutane and/or the tertiary chlorinated alkene 4-chloro-4-methyl-1-pentene. Alternatively, feed stream 15 can be a 1,3-dichloro-1-propene product having similar purity levels to Telone II® or even having lower purity levels. In this embodiment, feed stream 15 can be derived at least in part from an associated same-site process of making a mixed cis- and trans-1,3-dichloro-1-propene product, such as a commercial process for making Telone II®. System 10 is used to increase the purity level of the Telone II® product.

In another embodiment, feed stream 15 comprises a byproduct fraction of an allyl chloride manufacturing plant that includes cis- and trans-1,3-dichloro-1-propene and various other byproducts of the allyl chloride manufacturing plant that separate into the 1,3-dichloro-1-propene fraction. For example, feed stream 15 can be derived at least in part from an associated same-site process for making allyl chloride. An example of such a suitable feed stream is stream 26 of the allyl chloride process depicted in FIG. 1 of International Application Number PCT/US95/14354, published as International Publication Number WO 97/03035, which is incorporated herein by reference in its entirety. Stream 26, or a mixture similarly composed of 1,3-dichloro-1-propene and tertiary chlorinated alkanes and/or tertiary chlorinated alkenes, is referred to herein as "Telone crude," and typically includes cis- and trans-1,3-dichloro-1-propene and at least one tertiary chlorinated alkane and/or tertiary chlorinated alkene impurity, such as, for example, the tertiary chlorinated alkane 2-chloro-2-methylepentane, the tertiary chlorinated alkane 2-chloro-2,3-dimethylbutane and/or the tertiary chlorinated alkene 4-chloro-4-methyl-1-pentene.

In the process depicted in FIG. 1, purified 1,3-dichloro-1-propene product 64 is produced by a multi-step process including a reaction that converts tertiary chlorinated alkane and/or tertiary chlorinated alkene impurities to corresponding unchlorinated or less-chlorinated alkenes and hydrogen chloride, and a plurality of distillation separation treatments. Specifically, feed stream 15 is fed into catalytic reactor 20 that defines a reaction chamber (also referred to herein as "dehydrochlorination reaction zone" or "reaction zone"), where it is contacted with a sorbent-type catalyst to convert tertiary chlorinated alkanes and/or tertiary chlorinated alkenes in feed stream 15 to corresponding unchlorinated or less-chlorinated alkenes and hydrogen chloride. Reaction temperatures, pressures and other reaction parameters can be as described above, provided that the reaction temperature in this embodiment is preferably from about 20 to about 130° C. and the pressure is preferably from about 5 to about 30 psia. In another embodiment, the temperature is from about 80 to about 120° C. In yet another embodiment, the temperature is from about 100 to about 110° C. In still another embodiment, the pressure is from about 10 to about 25 psia. In still yet another embodiment, the pressure is from about 14 to about 20 psia.

Catalytic reactor 20 is also configured to receive optional stripping gas flow stream 22 and to pass a stripping gas through the reaction chamber. The stripping gas operates to remove the corresponding unchlorinated or less-chlorinated alkene and hydrogen chloride reaction products from the reaction chamber of catalytic reactor 20, thereby helping to drive the equilibrium of the reaction toward the products. After passage through the reaction chamber of reactor 20, the stripping gas can be processed to remove hydrogen chloride and other reaction products entrained therein, and can optionally be recycled through the reaction chamber. In other embodiments, stripping gas flow stream 22 is absent. Reaction zone effluent 24 (also referred to herein as "phase 2 reaction mixture 24") exits reactor 20.

Reaction zone effluent 24 exiting reactor 20 includes a reduced concentration of tertiary chlorinated alkane and/or tertiary chlorinated alkene impurities compared to feed stream 15. Reaction zone effluent is then conveyed to vapor liquid separator and cooler 30 to separate components of reaction zone effluent 24 into first gaseous lights fraction 32, which can be recovered or disposed of via any conventional means, for example, by incineration, and first liquid fraction 34, which includes cis- and trans-1,3-dichloropropene and distillable impurities.

First liquid fraction 34 is then fed into first distillation separator 40, also referred to herein as the "trans distillation column" or "trans column," which is effective to separate and purify the higher boiling trans isomer of 1,3-dichloro-1-propene by removing a low boiling component 44 containing the cis-isomer and impurities from the top of separator 40 and recovering purified trans-1,3-dichloro-1-propene 46 from separator 40 as a high boiling component. In a case where feed stream 15 includes other low boiling other components, such as, for example, $C_3$ compounds or other low boiling other components, these are separated and recovered together with the cis-isomer in low boiling component 44. Separator 40 is also effective to separate tar fraction 48, which can be recovered from the bottom of separator 40 and disposed of via any conventional means, for example, by incineration.

First distillation separator 40 can be a conventional distillation column, also referred to in the industry as a distillation unit or a distillation tower. In the purification scheme depicted in FIG. 1, first distillation separator 40 is operated at a distillation temperature effective to separate the cis and trans isomers of 1,3-dichloro-1-propene from one another. In one embodiment, the distillation temperature of first distillation separator 40 is a temperature of from about 20 to about 110° C. In another embodiment, the distillation temperature of first distillation separator 40 is a temperature of from about 50 to about 90° C. The pressure is preferably a medium to deep vacuum. For example, in one embodiment, the pressure for distillation in separator 40 is a pressure of from about 30 mmHg to about 760 mmHg. In another embodiment, the pressure is from about 330 to about 370. In one embodiment, first distillation separator 40 is a distillation tower having from about 20 to about 90 equilibrium stages. In another embodiment, first distillation separator 40 is a distillation tower having from about 60 to about 80 equilibrium stages. In alternate embodiments, first distillation separator 40 can be set up for use in a batch distillation system or a continuous distillation system.

The cis isomer of 1,3-dichloro-1-propene and the low boiling impurities present in first liquid fraction 34 are separated and recovered from the top of first distillation separator 40. As used in connection with separator 40 of this embodiment, the term "low boiling" refers to compounds having boiling points lower than the boiling point of the trans isomer of 1,3-dichloro-1-propene, which tend to separate with the cis isomer in first distillation separator 40. Residual high boiling component 46 comprises the purified trans-isomer. In the embodiment depicted in FIG. 1, first distillation separator 40 is also configured to remove remaining lights from fraction 34 via second gaseous lights fraction 42 and to remove tars from fraction 34, both of which can be disposed of via any conventional means.

Low boiling component 44 containing the cis-isomer recovered from first distillation separator 40 is then conveyed to second distillation separator 50, also referred to herein as the "cis distillation column" or "cis column," which is effective to purify the cis isomer of 1,3-dichloro-1-propene present in component 44 by removing mid-boiling impurities 56 from the bottom of separator 50 and removing third gaseous lights fraction 52 from the top of separator 50, both of which can be disposed of via any conventional means. As used in connection with separator 50 of this embodiment, the term "mid-boiling impurities" refers to compounds having boiling points higher than the boiling point of the cis isomer of 1,3-dichloro-1-propene, which can be separated from the cis isomer by accumulating in the bottom of separator 50. Purified cis-1,3-dichloro-1-propene is recovered from second distillation separator 50 in fraction 54. Second distillation separator 50, like separator 40, can be a conventional distillation column. In one embodiment, the distillation temperature of second distillation separator 50 is a temperature of from about 20 to about 110° C. In another embodiment, the distillation temperature of second distillation separator 50 is a temperature of from about 50 to about 100° C. The pressure is preferably a medium to deep vacuum. For example, in one embodiment, the pressure for distillation in separator 50 is a pressure of from about 30 to about 760 mmHg. In another embodiment, the pressure is from about 520 to about 560 mmHg. In one embodiment, second distillation separator 50 is a distillation tower. There is no particular limit to the theoretical plate number of the distillation tower used as second distillation separator 50. However, in one embodiment, second distillation separator 50 is a distillation tower having from about 20 to about 90 equilibrium stages. In another embodiment, second distillation separator 50 is a distillation tower having from about 55 to about 75 equilibrium stages. In alternate embodiments, second distillation separator 50 can be set up for use in a batch distillation system or a continuous distillation system.

Purified trans-1,3-dichloro-1-propene 46 and purified cis-1,3-dichloro-1-propene 54 are then fed to mixer 60, where they are mixed in predetermined proportions to provide product 64, which is a mixture of purified cis- and trans-1,3-dichloro-1-propene that possesses known utility as a soil fumigant and nematocide. For example, product 64 can be a more highly purified commercial grade Telone II® product. In other embodiments, purified trans-1,3-dichloro-1-propene 46 and purified cis-1,3-dichloro-1-propene 54 are not mixed, but are instead used, sold, shipped or stored separately. For purposes of the present description, it is to be understood that the term "purified" does not connote that a given compound or fraction is entirely free from impurities. Rather, this term is intended to refer to a degree of purity higher than a reference material, such as, for example, a mixture that is fed into a distillation separator.

Figure 2:
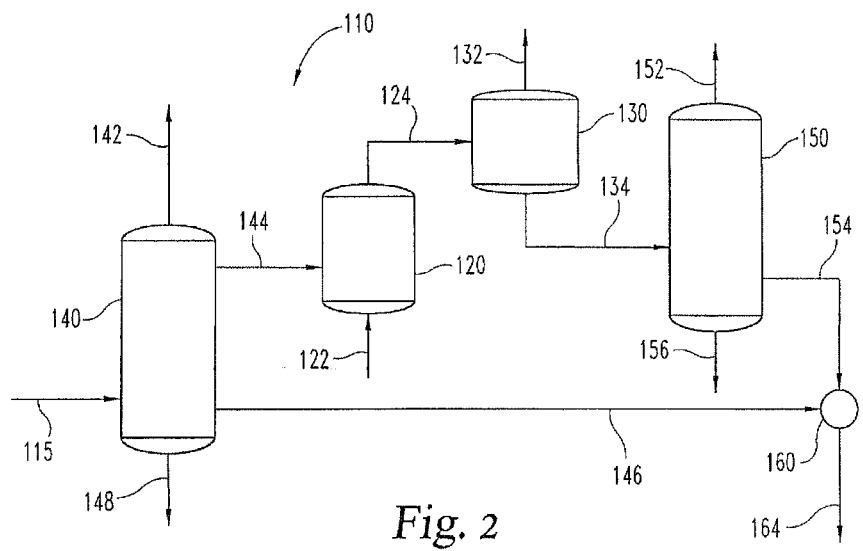
FIG. 2 is a schematic view of a 1,3-dichloro-1-propene purification system in accordance with another embodiment of the present application.

Because tertiary chlorinated alkane and/or tertiary chlorinated alkene impurities commonly found in a Telone crude feed stream have distillation profiles similar to cis-1,3-dichloro-1-propene, they tend to separate with the cis stream when distilled without prior dehydrochlorination. Therefore, the present application also contemplates placement of a dehydrochlorination reactor at a different location in the process. With reference to the embodiment depicted in FIG. 2, for example, dehydrochlorination reactor 120 is positioned after first distillation separator 140 (i.e., after the trans column). More specifically, feed stream 115 is fed into first distillation separator 140, which is effective to separate and purify the higher boiling trans isomer of 1,3-dichloro-1-propene by removing a low boiling component 144 containing the cis isomer and impurities from the top of separator 140 and recovering purified trans-1,3-dichloro-1-propene 146 from separator 140 as a high boiling component. Tertiary chlorinated alkanes and/or tertiary chlorinated alkenes present in feed stream 115 separate with cis isomer component 144. In a case where feed stream 115 includes other low boiling other components, such as, for example, $C_3$ compounds or other low boiling components, these are also separated and recovered together with the cis-isomer in low boiling component 144 or as first gaseous lights fraction 142. Separator 140 is also effective to separate tar fraction 148, which can be recovered from the bottom of separator 140.

First distillation separator 140, like separator 40 in FIG. 1, can be a conventional distillation column, can have a configuration as described above in connection with separator 40, and can be operated at similar distillation temperatures and pressures as described above in connection with separator 40. In alternate embodiments, first distillation separator 140 can be set up for use in a batch distillation system or a continuous distillation system.

As stated above, the cis isomer of 1,3-dichloro-1-propene and the low boiling impurities, including tertiary chlorinated alkanes and/or tertiary chlorinated alkenes, are present in low boiling component 144. As used in connection with separator 140 of this embodiment, the term "low boiling" refers to compounds having boiling points lower than the boiling point of the trans isomer of 1,3-dichloro-1-propene, which tend to separate with the cis isomer fraction 144 in first distillation separator 140. In the high boiling component 146, the purified trans-isomer will be contained. In the embodiment depicted in FIG. 2, first distillation separator 140 is also configured to remove remaining lights from feed stream 115 via first gaseous lights fraction 142 and to remove tars from feed stream 115 in distillation separator 140.

Component 144, which includes the cis isomer of 1,3-dichloro-1-propene and also impurities, including tertiary chlorinated alkane and/or tertiary chlorinated alkene impurities, is fed into a reaction chamber of catalytic reactor 120, where it is contacted with a sorbent-type catalyst to convert tertiary chlorinated alkanes and/or tertiary chlorinated alkenes in component 144 to corresponding unchlorinated or less-chlorinated alkenes and hydrogen chloride.

The reaction of tertiary chlorinated alkanes and/or tertiary chlorinated alkenes is carried out at a temperature and pressure, and under conditions similar to those described above in connection with reactor 20. Catalytic reactor 120 is also optionally configured to receive stripping gas flow stream 122 and to pass the stripping gas through the reaction chamber, thereby removing reaction products in the vapor phase that are produced in catalytic reactor 120. After passage through the reaction chamber of reactor 120, the stripping gas can then be processed to remove hydrogen chloride and other reaction products entrained therein, and can optionally be recycled through the reaction chamber. In other embodiments, stripping gas flow stream 122 is absent. Reaction zone effluent 124 (also referred to herein as "phase 2 reaction mixture 124") exits reactor 120.

Reaction zone effluent 124 exiting reactor 120 includes a reduced amount of tertiary chlorinated alkane and/or tertiary chlorinated alkene impurities compared to component 144. Reaction zone effluent is then conveyed to vapor liquid separator and cooler 130 to separate components of reaction zone effluent 124 into first gaseous lights fraction 132 and rough cis fraction 134, which includes cis-1,3-dichloropropene and distillable impurities.

Rough cis fraction 134 is then fed into second distillation separator 150, also referred to herein as the "cis distillation column" or "cis column," which is effective to purify the cis isomer of 1,3-dichloro-1-propene present in fraction 134 by removing mid-boiling impurities 156 from the bottom of separator 150 and removing third gaseous lights fraction 152 from the top of separator 150. As used in connection with separator 150 of this embodiment, the term "mid-boiling impurities" refers to compounds having boiling points higher than the boiling point of the cis isomer of 1,3-dichloro-1-propene, which can be separated from the cis isomer by accumulating in the bottom of separator 150. Purified cis-1,3-dichloro-1-propene 154 is recovered from second distillation separator 150.

Second distillation separator 150, like separator 50 in FIG. 1, can be a conventional distillation column, can have a configuration as described above in connection with separator 50, and can be operated at similar distillation temperatures and pressures as described above in connection with separator 50. In alternate embodiments, second distillation separator 150 can be set up for use in a batch distillation system or a continuous distillation system.

Purified trans-1,3-dichloro-1-propene 146 and purified cis-1,3-dichloro-1-propene 154 are then fed to mixer 160, where they are mixed in predetermined proportions to provide product 164, such as, for example, a purified Telone II® product. In other embodiments, purified trans-1,3-dichloro-1-propene 146 and purified cis-1,3-dichloro-1-propene 154 are not mixed, but are instead used, sold, shipped or stored separately.

In the systems described above, the tertiary chlorinated alkane reactor is positioned in a process flow stream either before or after a trans column. One of the advantages of the dehydrochlorination catalysts describe herein is that the conversion of tertiary chlorinated alkanes and/or tertiary chlorinated alkenes to corresponding unchlorinated or less-chlorinated alkenes and hydrogen chloride can occur in the liquid or gaseous phase. Thus, a variety of embodiments are possible in which the reaction is caused to occur within one or more of the distillation columns during distillation processing. For example, in the embodiment depicted in FIG. 3, system 210 includes reactor 220 positioned within first distillation separator 240. In this embodiment, reactor 220 can be a packed bed reactor or can comprise baffles or other structures that are made of the catalytic material and that are positioned within first distillation separator 240.

Figure 3:
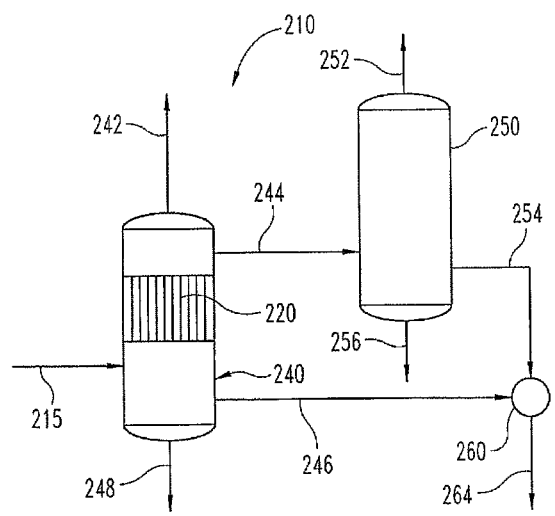
FIG. 3 is a schematic view of a 1,3-dichloro-1-propene purification system in accordance with another embodiment of the present application.

In operation of the system set forth in FIG. 3, feed stream 215 is fed into first distillation separator 240 (trans column) having reactor 220 positioned therein. Separator 240 is effective to separate and purify the higher boiling trans isomer of 1,3-dichloro-1-propene while at the same time converting tertiary chlorinated alkanes and/or tertiary chlorinated alkenes in feed stream 215 to corresponding unchlorinated or less-chlorinated alkenes and hydrogen chloride. Low boiling component 244 containing the cis-isomer and impurities, including the newly generated products of the catalyzed dehydrochlorination reaction of tertiary chlorinated alkanes and/or tertiary chlorinated alkenes in reactor 220, are recovered from the top of separator 240 and purified trans-1,3-dichloro-1-propene 246 is recovered from separator 240 as a high boiling component. In a case where feed stream 215 includes other low boiling other components, such as, for example, $C_3$ compounds or other low boiling other components, these are separated and recovered together with the cis-isomer in low boiling component 244. Separator 240 is also effective to separate first gaseous light fraction 242 from the top of separator 240 and tar fraction 248, which can be recovered from the bottom of separator 240.

In the purification scheme described in connection with FIG. 3, first distillation separator 240, like separator 40 in FIG. 1, can be similar to a conventional distillation column, can have a configuration as described above in connection with separator 40, and can be operated at similar distillation temperatures and pressures as described above in connection with separator 40, with the proviso that separator 240 is modified to include therein reactor 220, which can comprise, for example, a packed bed of sorbent-type catalyst particles or, alternatively, baffles made of sorbent-type catalyst materials. In alternate embodiments, first distillation separator 240 can be set up for use in a batch distillation system or a continuous distillation system.

The cis isomer of 1,3-dichloro-1-propene and the low boiling impurities, including alkenes and hydrogen chloride produced by catalytic dehydrochlorination of tertiary chlorinated alkanes and/or tertiary chlorinated alkenes in reactor 220, are present in low boiling component 244 separated and recovered from the top of first distillation separator 240. As used in connection with separator 240 of this embodiment, the term "low boiling" refers to compounds having boiling points lower than the boiling point of the trans isomer of 1,3-dichloro-1-propene, which low boiling compounds tend to separate with the cis isomer fraction 244 in first distillation separator 240. In the high boiling component 246, the purified trans-isomer will be contained. In the embodiment depicted in FIG. 3, first distillation separator 240 is also configured to remove lights from feed stream 215 via first gaseous lights fraction 242 and to remove tars from feed stream 215 in distillation separator 240.

As stated above, low boiling component 244 recovered from separator 240 includes the cis isomer of 1,3-dichloro-1-propene and also impurities, including alkenes and hydrogen chloride produced by the catalytic dehydrochlorination of tertiary chlorinated alkanes and/or tertiary chlorinated alkenes in reactor 220. Component 244, also referred to as "rough cis fraction 244," is fed into second distillation separator 250, also referred to herein as the "cis distillation column" or "cis column," which is effective to purify the cis isomer of 1,3-dichloro-1-propene present in fraction 244 by removing mid-boiling impurities 256 from the bottom of separator 250 and removing second gaseous lights fraction 252 from the top of separator 250. As used in connection with separator 250 of this embodiment, the term "mid-boiling impurities" refers to compounds having boiling points higher than the boiling point of the cis isomer of 1,3-dichloro-1-propene, which mid boiling impurities can be separated from the cis isomer by accumulating in the bottom of separator 250. Purified cis-1,3-dichloro-1-propene 254 is recovered from second distillation separator 250.

Second distillation separator 250, like separator 50 in FIG. 1, can be a conventional distillation column, can have a configuration as described above in connection with separator 50, and can be operated at similar distillation temperatures and pressures as described above in connection with separator 50. In alternate embodiments, second distillation separator 250 can be set up for use in a batch distillation system or a continuous distillation system.

Purified trans-1,3-dichloro-1-propene 246 and purified cis-1,3-dichloro-1-propene 254 are then fed to mixer 260, where they are mixed in predetermined proportions to provide product 264, such as, for example, a more highly purified Telone II® product. In other embodiments, purified trans-1,3-dichloro-1-propene 246 and purified cis-1,3-dichloro-1-propene 254 are not mixed, but are instead used, sold, shipped or stored separately.

Figure 4:
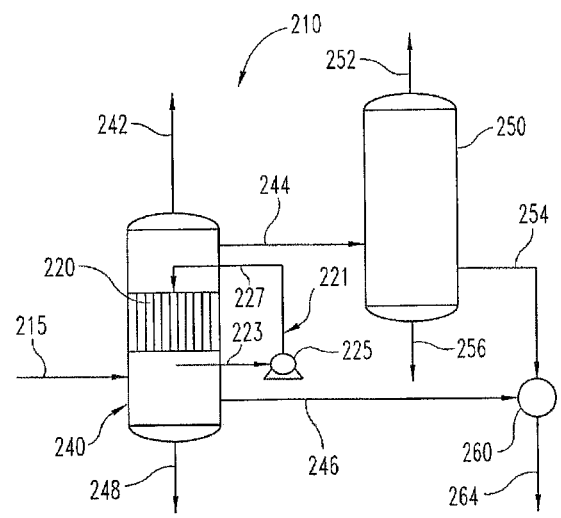
FIG. 4 is a schematic view of a 1,3-dichloro-1-propene purification system in accordance with another embodiment of the present application.

System 210 can also include optional liquid recirculation loop 221, as depicted in FIG. 4, to enhance the yield of the dehydrochlorination reaction. Optional liquid recirculation loop 221 includes flow path 223 for extracting a portion of the distilling mixture from a position in separator 240 beneath reactor 220 and flow path 227 for returning the distilling mixture to a position in separator 240 above reactor 220, using pump 225. Optional recirculation loop, when present, provides an opportunity for any tertiary chlorinated alkane and/or tertiary chlorinated alkene impurities that may have passed through reactor 220 without being converted to corresponding unchlorinated or less-chlorinated alkenes and hydrogen chloride to pass again through reactor 220, thereby providing a further opportunity for conversion by dehydrochlorination, and ultimately increasing the purity of product 264.

Figure 5:
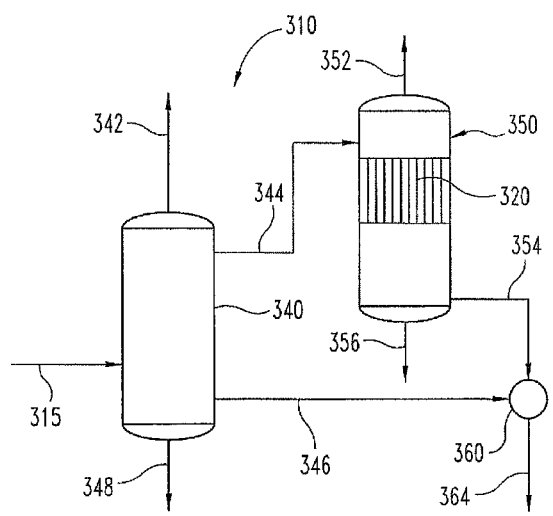
FIG. 5 is a schematic view of a 1,3-dichloro-1-propene purification system in accordance with another embodiment of the present application.

System 310 depicted in FIG. 5 includes reactor 320 positioned within second distillation separator 350. In this embodiment, reactor 320 can be a packed bed reactor or can comprise baffles or other structures that are made of the catalytic material and that are positioned within second distillation separator 350. In operation of the system set forth in FIG. 5, feed stream 315 is fed into first distillation separator 340, which, like separator 40 in FIG. 1, can be a conventional distillation column, can have a configuration as described above in connection with separator 40, and can be operated at similar distillation temperatures and pressures as described above in connection with separator 40. In alternate embodiments, first distillation separator 340 can be set up for use in a batch distillation system or a continuous distillation system.

First distillation separator 340 is effective to separate and purify the higher boiling trans isomer of 1,3-dichloro-1-propene by removing a low boiling component 344 containing the cis isomer and impurities from the top of separator 340 and recovering purified trans-1,3-dichloro-1-propene 346 from separator 340 as a high boiling component. Tertiary chlorinated alkane and/or tertiary chlorinated alkene impurities present in feed stream 315 separate with cis isomer component 344. In a case where feed stream 315 includes other low boiling other components, such as, for example, $C_3$ compounds or other low boiling components, these are separated and recovered together with the cis-isomer in low boiling component 344 or as first gaseous lights fraction 342. Separator 340 is also effective to separate tar fraction 348, which can be recovered from the bottom of separator 340.

Low boiling component 344 recovered from separator 340, which includes the cis isomer of 1,3-dichloro-1-propene and also impurities, including tertiary chlorinated alkane and/or tertiary chlorinated alkene impurities, is fed into second distillation separator 350 (cis column), which has reactor 320 positioned therein. Separator 350 is effective to separate and purify the lower boiling cis isomer of 1,3-dichloro-1-propene while at the same time converting tertiary chlorinated alkane and/or tertiary chlorinated alkene impurities in component 344 to corresponding unchlorinated or less-chlorinated alkenes and hydrogen chloride. Purified cis-1,3-dichloro-1-propene is separated and recovered in separator 350 by removing mid-boiling impurities 356 from the bottom of separator 350 and removing second gaseous lights fraction 352 from the top of separator 350. The newly generated alkenes and hydrogen chloride produced by the catalyzed reaction of tertiary chlorinated alkane and/or tertiary chlorinated alkene impurities in reactor 320, are recovered from the top of separator 350 in second gaseous lights fraction 352.

In the purification scheme described in connection with FIG. 5, second distillation separator 350, like separator 50 in FIG. 1, can be a conventional distillation column, can have a configuration as described above in connection with separator 50, and can be operated at similar distillation temperatures and pressures as described above in connection with separator 50, with the proviso that separator 350 is modified to include therein reactor 320, which can comprise, for example, a packed bed of sorbent-type catalyst particles or, alternatively, baffles made of sorbent-type catalyst materials. In alternate embodiments, first distillation separator 350 can be set up for use in a batch distillation system or a continuous distillation system.

Purified trans-1,3-dichloro-1-propene 346 and purified cis-1,3-dichloro-1-propene 354 are then fed to mixer 360, where they are mixed in predetermined proportions to provide product 364, such as, for example, a more highly purified Telone II® product. In other embodiments, purified trans-1,3-dichloro-1-propene 346 and purified cis-1,3-dichloro-1-propene 354 are not mixed, but are instead used, sold, shipped or stored separately.

Figure 6:
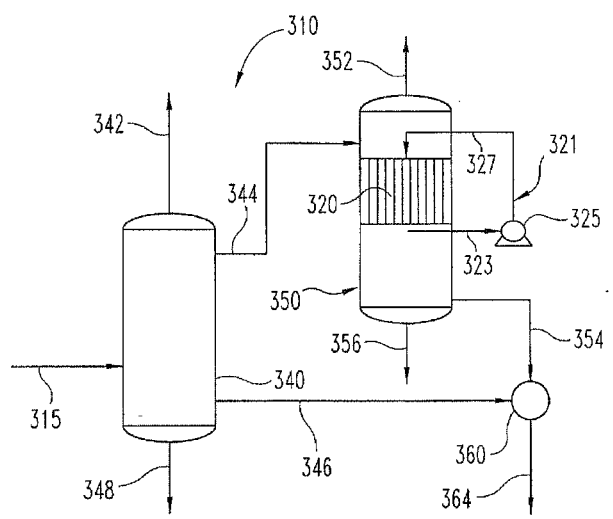
FIG. 6 is a schematic view of a 1,3-dichloro-1-propene purification system in accordance with another embodiment of the present application.

System 310 can also include optional liquid recirculation loop 321, as depicted in FIG. 6, to enhance the progress of the dehydrochlorination reaction. Optional liquid recirculation loop 321 includes flow path 323 for extracting a portion of the distilling mixture from a position in separator 350 beneath reactor 320 and flow path 327 for returning the distilling mixture to a position in separator 350 above reactor 320, using pump 325. Optional recirculation loop, when present, provides an opportunity for any tertiary chlorinated alkane and/or tertiary chlorinated alkene impurities that may have passed through reactor 320 without being converted to corresponding unchlorinated or less-chlorinated alkenes and hydrogen chloride to pass again through reactor 320, thereby providing a further opportunity for conversion by dehydrochlorination, and ultimately increasing the purity of product 364.

Figure 7:
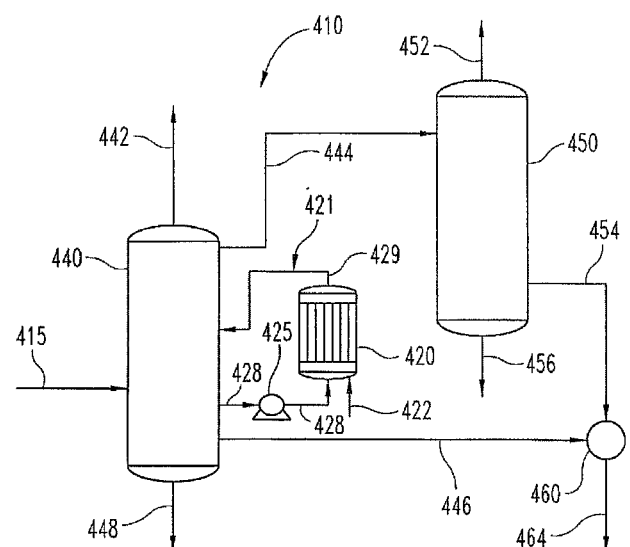
FIG. 7 is a schematic view of a 1,3-dichloro-1-propene purification system in accordance with another embodiment of the present application.
Figure 8:
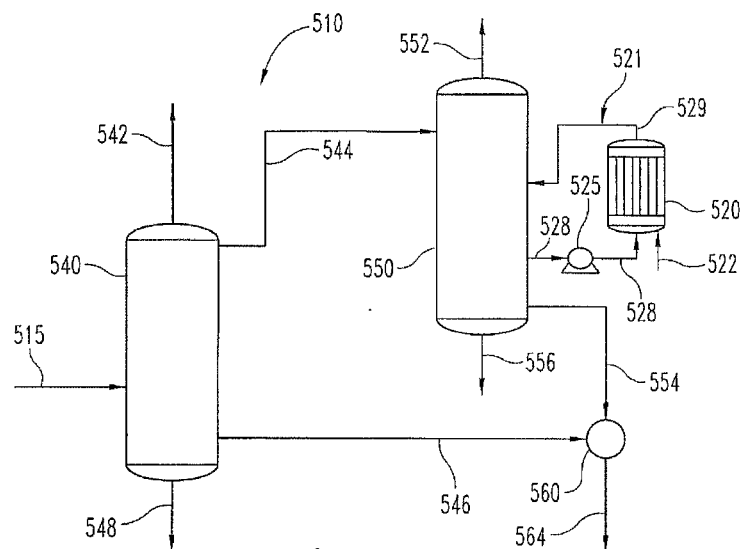
FIG. 8 is a schematic view of a 1,3-dichloro-1-propene purification system in accordance with another embodiment of the present application.

Systems 410 and 510 depicted in FIGS. 7 and 8, respectively, include first distillation separators 440, 540, which, like separator 40 in FIG. 1, can be conventional distillation columns, can have configurations as described above in connection with separator 40, and can be operated at similar distillation temperatures and pressures as described above in connection with separator 40. In alternate embodiments, first distillation separators 440, 540 can be set up for use in a batch distillation system or a continuous distillation system. Systems 410 and 510 also include second distillation separators 450, 550, which, like separator 50 in FIG. 1, can be a conventional distillation column, can have a configuration as described above in connection with separator 50, and can be operated at similar distillation temperatures and pressures as described above in connection with separator 50. In alternate embodiments, second distillation separators 450, 550 can be set up for use in a batch distillation system or a continuous distillation system.

System 410 depicted in FIG. 7, includes reactor circuit 421 configured to extract distilling mixture from separator 440 (trans column), pass the distilling mixture in contact with a dehydrochlorination catalyst, and return the dehydrochlorination-treated distilling mixture into separator 440. More specifically, reactor circuit 421 includes flow stream 428, with pump 425, for extracting a portion of the distilling mixture from separator 440 and feeding the extracted distilling mixture into catalytic reactor 420 that defines a reaction chamber, where it is contacted with a sorbent-type catalyst to convert tertiary chlorinated alkane and/or tertiary chlorinated alkene impurities in flow stream 428 to corresponding unchlorinated or less-chlorinated alkenes and hydrogen chloride.

Catalytic reactor 420 is also configured to receive optional stripping gas flow stream 422 and to pass a stripping gas through the reaction chamber, thereby removing reaction products in the vapor phase that are produced in catalytic reactor 420. After passage through the reaction chamber of reactor 420, the stripping gas can then be processed to remove hydrogen chloride and other reaction products entrained therein. In other embodiments, stripping gas flow stream 422 is absent.

Reactor circuit 421 also includes return flow path 429 for returning the dehydrochlorination-treated distilling mixture to separator 440 for further distillation processing. As used herein, the term "dehydrochlorination-treated distilling mixture" refers to a mixture that has been contacted with a dehydrochlorination catalyst as described herein, and which includes a reduced amount of tertiary chlorinated alkane and/or tertiary chlorinated alkene impurities compared to flow stream 428. As a result, rough cis fraction 444 separated and recovered from separator 440 has a lower tertiary chlorinated alkane and/or tertiary chlorinated alkene content than it would have in the absence of reactor circuit 421, and purified cis fraction 454 is in a more highly purified form than would be produced in the absence of reactor circuit 421.

System 510 depicted in FIG. 8, includes reactor circuit 521 configured to extract distilling mixture from separator 550 (cis column), pass the distilling mixture in contact with a dehydrochlorination catalyst, and return the dehydrochlorination-treated distilling mixture into separator 550. More specifically, reactor circuit 521 includes flow stream 528, with pump 525, for extracting a portion of the distilling mixture from separator 550 and feeding the extracted distilling mixture into catalytic reactor 520 that defines a reaction chamber, where it is contacted with a sorbent-type catalyst to convert tertiary chlorinated alkane and/or tertiary chlorinated alkene impurities in flow stream 528 to corresponding unchlorinated or less-chlorinated alkenes and hydrogen chloride.

Catalytic reactor 520 is also configured to receive optional stripping gas flow stream 522 and to pass a stripping gas through the reaction chamber, thereby removing reaction products in the vapor phase that are produced in catalytic reactor 520. After passage through the reaction chamber of reactor 520, the stripping gas can then be processed to remove hydrogen chloride and other reaction products entrained therein. In other embodiments, stripping gas flow stream 522 is absent.

Reactor circuit 521 also includes return flow path 529 for returning the dehydrochlorination-treated distilling mixture to separator 550 for further distillation processing. As used herein, the term "dehydrochlorination-treated distilling mixture" refers to a mixture that has been contacted with a dehydrochlorination catalyst as described herein, and which includes a reduced amount of tertiary chlorinated alkane and/or tertiary chlorinated alkene impurities compared to flow stream 528. As a result, purified cis fraction 554 has a lower tertiary chlorinated alkane and/or tertiary chlorinated alkene content than it would have in the absence of reactor circuit 521.

Figure 9:
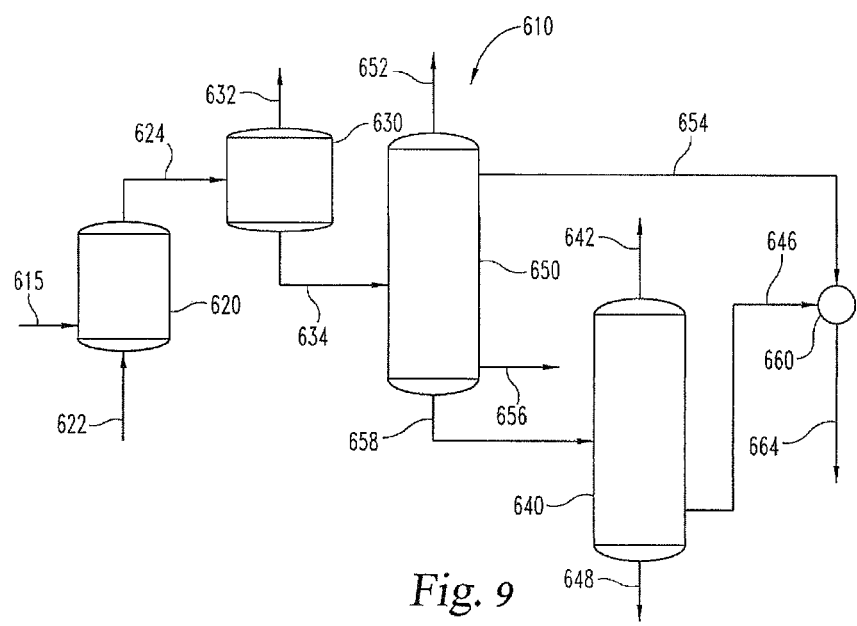
FIG. 9 is a schematic view of a 1,3-dichloro-1-propene purification system in accordance with another embodiment of the present application.

In other embodiments, dehydrochlorination treatments as described herein can be used in connection with purification schemes in which the cis column precedes the trans column in the distillation process. For example, with reference to FIG. 9, system 610 includes catalytic reactor 620 and vapor liquid separator and cooler 630 similar to catalytic reactor 20 and vapor liquid separator and cooler 30 described above in connection with system 10 depicted in FIG. 1. However, first liquid fraction 634 recovered from vapor liquid separator and cooler 634 is not fed into a trans column as is first liquid fraction 34 depicted in FIG. 1. Rather, first liquid fraction 634 is fed into cis column 650, which is effective to purify the cis isomer of 1,3-dichloro-1-propene present in first liquid fraction 634 into fraction 654 recovered from separator 650, removing mid-boiling impurities 656 from a lower position of separator 650, removing first gaseous lights fraction 652 from the top of separator 650, and collecting rough trans-1,3-dichloro-1-propene fraction 658 from the bottom of separator 650. As used in connection with this embodiment, the term "mid-boiling impurities" refers to compounds having boiling points higher than the boiling point of the cis isomer of 1,3-dichloro-1-propene and lower than the boiling point of the trans isomer of 1,3-dichloro-1-propene, which can be separated from the cis and trans isomers from a lower position of separator 650. In one embodiment, cis column 650 is operated at a temperature slightly below the boiling point of the trans isomer of 1,3-dichloro-1-propene and above the boiling point of the cis isomer of 1,3-dichloro-1-propene.

Rough trans-1,3-dichloro-1-propene fraction 658 is then fed into trans column 640, which is effective to separate and purify the higher boiling trans isomer of 1,3-dichloro-1-propene by removing a mid boiling and lights component 642 containing impurities from the top of trans column 640 and recovering purified trans-1,3-dichloro-1-propene 646 from column 640 as a high boiling component. Column 640 also separates tar fraction 648, which can be recovered from the bottom of column 640.

Purified trans-1,3-dichloro-1-propene 646 and purified cis-1,3-dichloro-1-propene 654 are then fed to mixer 660, where they are mixed in predetermined proportions to provide product 664, such as, for example, a more highly purified Telone II® product. In other embodiments, purified trans-1,3-dichloro-1-propene 646 and purified cis-1,3-dichloro-1-propene 654 are not mixed, but are instead used, sold, shipped or stored separately.

Figure 10:
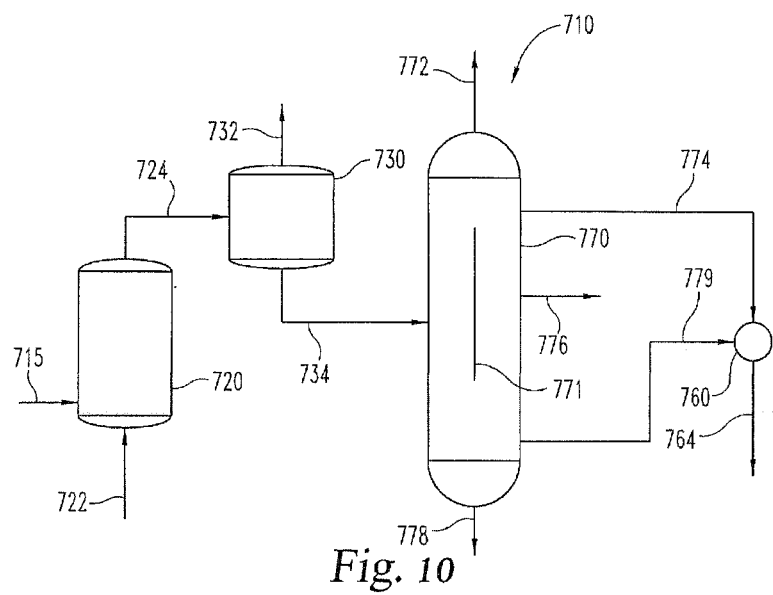
FIG. 10 is a schematic view of a 1,3-dichloro-1-propene purification system in accordance with another embodiment of the present application.

In still other embodiments, dehydrochlorination treatments as described herein can be used in connection with purification schemes in which the cis and trans distillation processes are conducted in a single dividing wall column. For example, with reference to FIG. 10, system 710 represents a system in which dehydrochlorination is performed prior to distillation in dividing wall distillation column 771. In system 710, feed stream 715 is fed into catalytic reactor 720 that defines a reaction chamber, where it is contacted with a sorbent-type catalyst to convert tertiary chlorinated alkane and/or tertiary chlorinated alkene impurities in feed stream 715 to corresponding unchlorinated or less-chlorinated alkenes and hydrogen chloride. The reaction of tertiary chlorinated alkanes and/or tertiary chlorinated alkenes is carried out at a temperature and pressure, and under conditions similar to those described above in connection with reactor 20 of FIG. 1. Catalytic reactor 720 is also configured to receive optional stripping gas flow stream 722 and to pass the stripping gas through the reaction chamber, thereby removing reaction products in the vapor phase that are produced in catalytic reactor 720. After passage through the reaction chamber of reactor 720, the stripping gas can then be processed to remove hydrogen chloride and other reaction products entrained therein. In other embodiments, stripping gas flow stream 722 is absent.

Reaction zone effluent 724 (also referred to herein as "phase 2 reaction mixture 724"), which exits reactor 720, includes a reduced amount of tertiary chlorinated alkane and/or tertiary chlorinated alkene impurities compared to component feed stream 715. Reaction zone effluent is then conveyed to vapor liquid separator and cooler 730 to separate components of reaction zone effluent 724 into first gaseous lights fraction 732 and distillation feed mixture 734, which includes cis- and trans-1,3-dichloropropene and distillable impurities.

Distillation feed mixture 734 is then fed into dividing wall distillation column 770. Column 770 can be of a type commercially available and known to persons of ordinary skill in the art. Briefly, column 770 includes internal barrier 771 that divides column into two distillation chambers. Column 770 is effective for separating distillation feed mixture 734 into multiple fractions. Specifically with reference to system 710, column 770 is effective to separate distillation feed mixture 734 into purified cis-1,3-dichloro-1-propene fraction 774 and purified trans-1,3-dichloro-1-propene fraction 779, while separating same from second lights fraction 772, mid-boiling impurity fraction 776 and tars fraction 778. Second lights fraction 772, mid-boiling impurity fraction 776 and tars fraction 778 can be disposed of via any conventional means.

Purified trans-1,3-dichloro-1-propene fraction 779 and purified cis-1,3-dichloro-1-propene fraction 774 are then fed to mixer 760, where they are mixed in predetermined proportions to provide a purified final product 764 that is useful as a pesticide, such as, for example, a purified Telone II® product. In other embodiments, purified trans-1,3-dichloro-1-propene fraction 779 and purified cis-1,3-dichloro-1-propene fraction 774 are not mixed, but are instead used, sold, shipped or stored separately.

Figure 11:
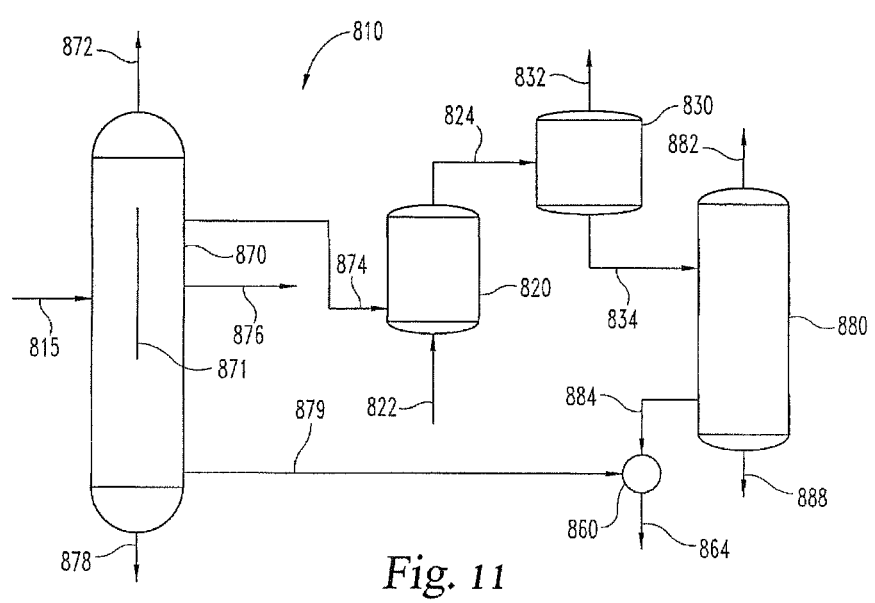
FIG. 11 is a schematic view of a 1,3-dichloro-1-propene purification system in accordance with another embodiment of the present application.

FIG. 11 depicts another embodiment in which a single dividing wall column is used; however, in system 810, dehydrochlorination is performed after distillation in the dividing wall column. Because tertiary chlorinated alkane and/or tertiary chlorinated alkene impurities tend to separate with the cis fraction, this embodiment features dehydrochlorination treatment of the cis fraction after separation in dividing wall column 870. More specifically, feed stream 815 is fed into dividing wall distillation column 870, which is effective to divide feed stream 815 into fraction 874, which includes cis-1,3-dichloro-1-propene and tertiary chlorinated alkane and/or tertiary chlorinated alkene impurities, and purified trans-1,3-dichloro-1-propene fraction 879. Fractions 874 and 879 are thus separated from first lights fraction 872, mid-boiling impurity fraction 876 and tars fraction 878. Column 870, like column 770 in FIG. 10, includes internal barrier 871 that divides column into two distillation chambers, can have a configuration as described above in connection with column 770, and can be operated at similar distillation temperatures and pressures as described above in connection with column 770. In alternate embodiments, dividing wall column 870 can be set up for use in a batch distillation system or a continuous distillation system. Second lights fraction 872, mid-boiling impurity fraction 876 and tars fraction 878 can be disposed of via any conventional means.

As stated above, tertiary chlorinated alkane and/or tertiary chlorinated alkene impurities present in feed stream 815 separate with the cis isomer in fraction 874. Fraction 874 is fed into a reaction chamber of catalytic reactor 820, where it is contacted with a sorbent-type catalyst to convert tertiary chlorinated alkane and/or tertiary chlorinated alkene impurities in fraction 874 to corresponding unchlorinated or less-chlorinated alkenes and hydrogen chloride. The reaction of tertiary chlorinated alkane and/or tertiary chlorinated alkene impurities is carried out at a temperature and pressure, and under conditions similar to those described above in connection with reactor 20. Catalytic reactor 820 is also configured to receive optional stripping gas flow stream 822 and to pass the stripping gas through the reaction chamber, thereby removing reaction products in the vapor phase that are produced in catalytic reactor 820. After passage through the reaction chamber of reactor 820, the stripping gas can then be processed to remove hydrogen chloride and other reaction products entrained therein. Reaction zone effluent 824 (also referred to herein as "phase 2 reaction mixture 824") exiting reactor 820 includes a reduced amount of tertiary chlorinated alkane and/or tertiary chlorinated alkene impurities compared to fraction 874. Reaction zone effluent 824 is then conveyed to vapor liquid separator and cooler 830 to separate reaction zone effluent 824 into first gaseous lights fraction 832 and rough cis fraction 834, which includes cis-1,3-dichloropropene and distillable impurities.

Rough cis fraction 834 is then fed into second distillation separator 880, also referred to herein as the "lights column," which is effective to purify the cis isomer of 1,3-dichloro-1-propene present in fraction 834 by removing mid-boiling impurities 888 from the bottom of separator 880 and removing third gaseous lights fraction 882 from the top of separator 880. As used in connection with separator 880 of this embodiment, the term "mid-boiling impurities" refers to compounds having boiling points higher than the boiling point of the cis isomer of 1,3-dichloro-1-propene, which can be separated from the cis isomer by accumulating in the bottom of separator 880. Purified cis-1,3-dichloro-1-propene 884 is recovered from second distillation separator 880.

Second distillation separator 880, like separator 50 in FIG. 1, can be a conventional distillation column, can have a configuration as described above in connection with separator 50, and can be operated at similar distillation temperatures and pressures as described above in connection with separator 50. In alternate embodiments, second distillation separator 880 can be set up for use in a batch distillation system or a continuous distillation system.

Purified trans-1,3-dichloro-1-propene fraction 879 and purified cis-1,3-dichloro-1-propene fraction 884 are then fed to mixer 860, where they are mixed in predetermined proportions to provide purified product 864, such as, for example, a more highly purified Telone II® product. In other embodiments, purified trans-1,3-dichloro-1-propene fraction 879 and purified cis-1,3-dichloro-1-propene fraction 884 are not mixed, but are instead used, sold, shipped or stored separately.

By the processes described herein, both the cis-isomer and the transisomer of 1,3-dichloro-1-propene can be obtained at high purity levels, such as, for example, at purity levels of at least 98%, more preferably at least 99%. Specifically, the impurity 2-chloro-2-methylpentane commonly present in Telone crude can be reduced to a level below 1000 ppm, the impurity 2-chloro-2,3-dimethylbutane commonly present in Telone crude can be reduced to a level below 1000 ppm and the impurity 4-chloro-4-methyl-l-pentene commonly present in Telone crude can be reduced to levels below 1000 ppm. indeed, impurity levels can be reduced to significantly lower than 1000 ppm using techniques described herein. The cis-isomer and the trans-isomer obtained by the processes described here can be used, for example, as soil fumigants to control nematodes. In addition to the embodiments depicted in FIGS. 1-11, the present application contemplates that additional unit processes can be added to the system as would occur to a person skilled in the art. For example and without limitation, when feed stream 15, 115, 215, 315, 415, 515, 615, 715, 815 comprises Telone crude or a similarly composed mixture, it may be desirable to subject the feed stream to a chlorination treatment prior to feeding the feed stream into a reactor or distillation column in accordance with the various embodiments. Additional optional treatment phases can include, for example, a primary tar removal treatment, which can be performed either before or after catalytic dehydrochlorination treatment, but preferably before distillation treatment; and/or a propane dichloride removal and purification treatment, which preferably occurs before catalytic dehydrochlorination treatment and before distillation treatment.

It is well known that before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide. In another aspect of the present application, therefore, there is provided a process that includes submitting data to a governmental authority in order to obtain product registration approval for a product comprising a purified cis-1,3-dichloro-1-propene fraction made in accordance with the processes of the present application, a purified trans-1,3-dichloro-1-propene fraction made in accordance with the processes of the present application or a purified 1,3-dichloro-1-propene mixture made in accordance with the processes of the present application Many other aspects and embodiments are also envisioned. For example, as a closing observation, the various processes of FIGS. 1-11 have been described particularly with regard to processes for removing tertiary chlorinated alkane and/or tertiary chlorinated alkene impurities from a feed stream including 1,3-dichloro-1-propene as a major component. Those skilled in the art will however readily appreciate that the processes of FIGS. 1-11 and the concepts embodied therein are more broadly applicable to the removal of tertiary halogenated hydrocarbon impurities from a wide variety of hydrocarbon compounds, and are especially applicable to the removal of tertiary halogenated hydrocarbon impurities from other halogenated hydrocarbons and/or from hydrocarbons having boiling points similar to (e.g., within about 5° C. of) one or more of the tertiary halogenated hydrocarbon impurities. Because the catalyzed dehydrohalogenation reactions described herein are selective for tertiary halogenated hydrocarbons having a beta hydrogen, the methods and systems described herein lend themselves well to the selective removal of tertiary halogenated hydrocarbons from other halogenated hydrocarbons.

As will be appreciated by a person skilled in the art in view of the above descriptions, in one aspect of the present application, there is provided a method for removing a tertiary chlorinated hydrocarbon impurity from 1,3-dichloro-1-propene that includes: (1) providing a first mixture comprising 1,3-dichloro-1-propene and a tertiary chlorinated hydrocarbon impurity; (2) contacting the first mixture containing the tertiary chlorinated hydrocarbon impurity with a dehydrochlorination catalyst effective to catalyze a conversion of the tertiary chlorinated hydrocarbon impurity to a corresponding unchlorinated or less-chlorinated unsaturated hydrocarbon and hydrogen chloride; and (3) distilling the 1,3-dichloro-1-propene to separate and recover a purified cis-1,3-dichloro-1-propene fraction and a purified trans-1,3-dichloro-1-propene fraction. The purified cis-1,3-dichloro-1-propene fraction and the purified trans-1,3-dichloro-1-propene fraction can optionally then be mixed in a predetermined ratio to provide a purified 1,3-dichloro-1-propene mixture. In one embodiment, first mixture containing the tertiary chlorinated hydrocarbon impurity is contacted with a dehydrochlorination catalyst by providing a reactor defining a reaction zone containing the catalyst and feeding the first mixture containing the tertiary chlorinated hydrocarbon impurity into the reaction zone in contact with the catalyst. In another embodiment, a stripping gas stream is also passed through the reaction zone. The tertiary chlorinated hydrocarbon can be, for example, a tertiary chlorinated alkane having a beta hydrogen or a tertiary chlorinated alkene having a beta hydrogen. The dehydrochlorination catalyst can be, for example, activated alumina, sintered alumina, activated clay, fumed silica or silica gel, or magnesium silicate. Alternatively, the dehydrochlorination catalyst can be, for example, $TiO_2$, $Al_2O_3$, $ZrO_2$, $AlPO_4$ or $Al_xSi_yO_z$, or one of these materials doped with a metal.

One embodiment comprises: first contacting the first mixture containing the tertiary chlorinated hydrocarbon with the dehydrochlorination catalyst to produce a second mixture comprising 1,3-dichloro-1-propene and the corresponding unchlorinated or less-chlorinated unsaturated hydrocarbon; and then distilling the second mixture to produce a purified cis-1,3-dichloro-1-propene fraction and a purified trans-1,3-dichloro-1-propene fraction. The distilling can include, for example: (1) feeding the second mixture into a first distillation separator; (2) recovering from the first distillation separator the purified trans-1,3-dichloro-1-propene fraction, a rough cis fraction, a second lights fraction and a tars fraction; (3) feeding the rough cis fraction into a second distillation separator; and (4) recovering from the second distillation separator the purified cis-1,3-dichloro-1-propene fraction, a third lights fraction and a mid-boiling impurities fraction. In another example, the distilling includes: (1) feeding the second mixture into a first distillation separator; (2) recovering from the first distillation separator the purified cis-1,3-dichloro-1-propene fraction, a rough trans-1,3-dichloro-1-propene fraction, a second lights fraction and a mid-boiling impurities fraction; (3) feeding the rough trans-1,3-dichloro-1-propene fraction into a second distillation separator; and (4) recovering from the second distillation separator the purified trans-1,3-dichloro-1-propene fraction, a third lights fraction and a tars fraction. In this example, the second distillation separator is also effective to separate mid-boiling compounds in rough trans-1,3-dichloro-1-propene fraction into third lights fraction. In yet another example, the distilling includes: (1) feeding the second mixture into a dividing wall column distillation separator; and (2) recovering from the separator the purified cis-1,3-dichloro-1-propene fraction, the purified trans fraction, a second lights fraction, a mid-boiling impurities fraction and a tars fraction.

In still another embodiment, the method includes: (1) distilling the first mixture containing the tertiary chlorinated hydrocarbon to produce a purified trans-1,3-dichloro-1-propene fraction and a cis-1,3-dichloro-1-propene fraction, the cis-1,3-dichloro-1-propene fraction including the tertiary chlorinated hydrocarbon impurity; (2) contacting the cis-1,3-dichloro-1-propene fraction containing the tertiary chlorinated hydrocarbon with the dehydrochlorination catalyst to produce a second mixture (phase 2 mixture) comprising cis-1,3-dichloro-1-propene and the corresponding unchlorinated or less-chlorinated unsaturated hydrocarbon; and (3) distilling the second mixture to produce a purified cis-1,3-dichloro-1-propene fraction. In one example, the distilling the first mixture containing the tertiary chlorinated hydrocarbon comprises feeding the first mixture into a dividing wall column distillation separator and recovering from the dividing wall column distillation separator the purified cis-1,3-dichloro-1-propene fraction, the purified trans fraction, a first lights fraction, a mid-boiling impurities fraction and a tars fraction; the contacting comprises feeding the cis-1,3-dichloro-1-propene fraction containing the tertiary chlorinated hydrocarbon impurity into a reactor defining a reaction zone containing the catalyst to produce the second mixture; and the distilling the second mixture comprises feeding the second mixture into a second separator and recovering from the second separator the purified cis-1,3-dichloro-1-propene, a second lights fraction and a mid-boiling impurities fraction. The method can also optionally include passing a stripping gas stream through the reaction zone.

A further embodiment includes: (1) distilling the first mixture containing the tertiary chlorinated hydrocarbon impurity to produce a purified trans-1,3-dichloro-1-propene fraction and a cis-1,3-dichloro-1-propene fraction, the cis-1,3-dichloro-1-propene fraction including at least one impurity; and (2) distilling the cis-1,3-dichloro-1-propene fraction containing the at least one impurity to produce a purified cis-1,3-dichloro-1-propene fraction. In this embodiment, the distilling the first mixture containing the tertiary chlorinated hydrocarbon impurity comprises feeding the first mixture into a distillation separator defining a distillation chamber, said distillation chamber having the dehydrochlorination catalyst positioned therein. In yet another variation of this embodiment, the distillation separator further comprises a recirculation loop configured to extract a fluid from the distillation chamber at a position below the dehydrochlorination catalyst and to return the fluid to the distillation chamber at a position above the dehydrochlorination catalyst.

Yet a further embodiment comprises: (1) distilling the first mixture containing the tertiary chlorinated hydrocarbon impurity to produce a purified trans-1,3-dichloro-1-propene fraction and a rough cis-1,3-dichloro-1-propene fraction, the rough cis-1,3-dichloro-1-propene fraction including at least one impurity; and (2) distilling the rough cis-1,3-dichloro-1-propene fraction to produce a purified cis-1,3-dichloro-1-propene fraction. In this embodiment, distilling the rough cis-1,3-dichloro-1-propene fraction comprises feeding the rough cis-1,3-dichloro-1-propene fraction into a distillation separator defining a distillation chamber, the distillation chamber having the dehydrochlorination catalyst positioned therein. In yet another variation of this embodiment, the distillation separator further comprises a recirculation loop configured to extract a fluid from the distillation chamber at a position below the dehydrochlorination catalyst and to return the fluid to the distillation chamber at a position above the dehydrochlorination catalyst.

Yet another embodiment is directed to a method that includes: (1) distilling the first mixture containing the tertiary chlorinated hydrocarbon impurity in a first distillation separator to produce a purified trans-1,3-dichloro-1-propene fraction and a rough cis-1,3-dichloro-1-propene fraction, the rough cis-1,3-dichloro-1-propene fraction including at least one impurity; (2) distilling the rough cis-1,3-dichloro-1-propene fraction in a second distillation separator to produce a purified cis-1,3-dichloro-1-propene fraction; (3) extracting a portion of a distilling mixture from the first distillation separator, the distilling mixture including at least a portion of the tertiary chlorinated hydrocarbon impurity; (4) contacting the distilling mixture with a dehydrochlorination catalyst effective to catalyze a conversion of the tertiary chlorinated hydrocarbon impurity in the distilling mixture to a corresponding unchlorinated or less-chlorinated unsaturated hydrocarbon and hydrogen chloride, thereby producing a dehydrochlorination-treated distilling mixture; and (5) returning the dehydrochlorination-treated distilling mixture to the first distillation separator.

Still another embodiment is directed to a method that includes: (1) distilling the first mixture containing the tertiary chlorinated hydrocarbon impurity in a first distillation separator to produce a purified trans-1,3-dichloro-1-propene fraction and a cis-1,3-dichloro-1-propene fraction, the cis-1,3-dichloro-1-propene fraction including at least one impurity; (2) distilling the cis-1,3-dichloro-1-propene fraction in a second distillation separator to produce a purified cis-1,3-dichloro-1-propene fraction; (3) extracting a portion of a distilling mixture from the second distillation separator, the distilling mixture including at least a portion of the tertiary chlorinated hydrocarbon impurity; (4) contacting the distilling mixture with a dehydrochlorination catalyst effective to catalyze a conversion of the tertiary chlorinated hydrocarbon impurity in the distilling mixture to a corresponding unchlorinated or less-chlorinated unsaturated hydrocarbon and hydrogen chloride, thereby producing a dehydrochlorination-treated distilling mixture; and (5) returning the dehydrochlorination-treated distilling mixture to the second distillation separator.

In another aspect of the present application, there is provided a method for removing a tertiary halogenated hydrocarbon impurity from a target hydrocarbon compound that includes: (1) providing a first mixture comprising a target hydrocarbon compound and a tertiary halogenated hydrocarbon impurity; (2) contacting the first mixture containing the tertiary halogenated hydrocarbon impurity with a dehydrohalogenation catalyst effective to catalyze a conversion of the tertiary halogenated hydrocarbon impurity to a corresponding unhalogenated or less-halogenated unsaturated hydrocarbon and hydrogen halide, thereby providing a modified mixture; and (3) distilling the modified mixture to separate and recover a purified target hydrocarbon compound.

In yet another aspect, the application provides a method for dehydrohalogenating a tertiary halogenated hydrocarbon that includes: (1) providing a catalytic reactor defining a reaction chamber, the reaction chamber containing a sorbent-type dehydrohalogenation catalyst effective to catalyze a reaction of a tertiary halogenated hydrocarbon to a corresponding unhalogenated or less halogenated unsaturated hydrocarbon; (2) conveying a fluid comprising a tertiary halogenated hydrocarbon into the reaction chamber and into contact with the catalyst to convert at least a portion of the tertiary halogenated hydrocarbon to a corresponding unhalogenated or less-halogenated unsaturated hydrocarbon and hydrogen halide; and (3) passing a stripping gas through the reaction chamber to remove at least a portion of the hydrogen halide from the reaction chamber.

In still another aspect of the application, there is provided a process that includes submitting data to a governmental authority in order to obtain product registration approval for a product that includes any one of the purified cis-1,3-dichloro-1-propene fractions described herein, any one of the purified trans-1,3-dichloro-1-propene fractions described herein, any one of the purified 1,3-dichloro-1-propene mixtures described herein or any one of the purified target hydrocarbons described herein.

Reference will now be made to the following Examples, which describe experimental work directed to the subject matter of the present application. It is understood that no limitation to the scope of the application is intended thereby. The Examples are intended to be illustrative, are provided solely to promote a full understanding of the concepts embodied in the application, and are not intended to be limiting or otherwise restrictive as to the nature and scope of the inventions set forth herein.

EXAMPLES

Example One

Batch Experiments

Experiment I

In a first set of experiments, at ambient temperature, approximately 3 ml of Telone II® was loaded on top of 0.3 g of various solid sorbent-type catalysts. The vials were shaken for 48 hours at room temperature, then sampled and analyzed by gas chromatography with a flame ionization detector. When compared to the starting Telone II sample, the material that was contacted with silicon oxide and aluminum oxide containing solids showed a substantial (i.e., up to 100%) reduction in concentration in the tertiary chlorinated alkanes and alkenes and an increase in their decomposition products. Carbon based adsorbents showed a negligible reduction in chlorinated alkane concentration.

Experiment II

A second set of batch tests focused on the aluminum and silicone oxide catalysts and repeated the procedure of Experiment I. Each vial was sampled and the samples analyzed by gas chromatography with a flame ionization detector after one, three and 24 hours to understand the reaction as a function of time. In a follow-up, the process was repeated with the used catalyst and fresh Telone II®. Both experiments showed significant reductions in tertiary chlorinated alkanes and alkenes with most of the silicon and aluminum adsorbents. It was discovered that the pH of the catalyst has an effect on the rate of the reaction.

Experiment III

The same procedure as Experiment II was repeated at 60° C. but over a much shorter time frame. Each vial was sampled and analyzed after 15, 45 and 180 minutes. The results showed an approximate doubling of the rate of reaction for every increase of 10° C.

Example Two

Reaction Flow Tests

A packed bed reactor was constructed to test the effects of continuous flow across a catalyst bed. The reactor consisted of a ¼ OD tube loaded with catalyst.

The exterior of the tube was jacketed with a recirculated heating fluid providing an isothermal temperature zone across the reactor. The feed was pumped into the reactor in upflow mode, with the option to add an inert gas flow before entering the reactor.

Experiment I

Approximately 3 grams of F-200 activated alumina catalyst were loaded in the reactor and Telone II® (with tertiary chlorinated hydrocarbons ranging from 950 to 2550 ppm)

was fed at 1 mL/min. The reactor was maintained at 90° C. without nitrogen flow. The initial results showed a stable reduction of about 12-21% for the tertiary chlorinated hydrocarbons after the reaction.

Experiment II

The reactor was again loaded with 3 grams of F-200 activated alumina, with a liquid feed of 1 mL/min of Telone II®. For this experiment, 10 standard cubic centimeters per minute (sccm) of nitrogen was also added to the reactor at 90° C. In this case, the conversion of the tertiary chlorinated hydrocarbons was increased to 45-55%

Experiment III

With the same set-up described in experiment II, the temperature in the reactor was increased to 105° C., leaving the liquid flow rate at 1 mL/min and the gas flow rate at 10 seem of nitrogen. The conversion of the tertiary chlorinated hydrocarbons increased to 75-95%.

Experiment IV

Three grams of silica gel (60-200 mesh, 100 Angstrom pore diameter) was loaded into the reactor. The catalyst was at 1 mL/min Telone II® flow, 10 seem nitrogen, reactor pressure of 25 psia, and at a reaction temperature of 125° C. The tertiary chlorinated hydrocarbon conversion ranged from 52 to 63% conversion under these conditions.

Experiment V

Experiments were performed over three grams of sintered alumina catalyst. In this case, the feed was composed of a high purity cis-1,3-dichloropropene stream with approximately 3500 ppm of tertiary chlorinated hydrocarbons present. The liquid feed flow rate was 0.25 mL/min and the nitrogen flow rate was 5 sccm. The steady-state conversion was approximately 85% after 6 hours on stream.

Example Three

Distillation and Reaction in Combination

Telone II® product was split into cis and trans fractions and further purified using an industrial scale distillation column in the Telone II production plant. As single isomer products are normally produced in this column, the only variation from the standard operation was to produce higher purity by slowing the operation and increasing waste. The resulting purified isomers batches were mixed to produce a 50/50 to 60/40 mix of cis and trans isomers for feeding into the reactor described in the Reaction Flow Test section above. The reactor conditions were varied (temperature, stripping gas flow) such that 2-chloro-2-methylpentane concentrations in the reactor effluent were reduced to below 1000 ppm from 1200-2000 ppm. This material was then stripped of the reaction by-products (lights) in a 2" diameter batch distillation column.

While multiple embodiments of the invention have been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected. Any theory, mechanism of operation, proof, or finding stated herein is meant to further enhance understanding of the present application and is not intended to make the present application in any way dependent upon such theory, mechanism of operation, proof, or finding. It should be understood that any use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. All patents, patent applications, and publications references herein are hereby incorporated by reference, each in its entirety.

What is claimed is:

1. A method for removing a tertiary halogenated hydrocarbon impurity from a target hydrocarbon compound, comprising:
    providing a first mixture comprising a target hydrocarbon compound and a tertiary halogenated hydrocarbon impurity;
    feeding the first mixture containing the tertiary halogenated hydrocarbon impurity with into a reactor defining a reaction zone and containing a dehydrohalogenation catalyst effective to catalyze a conversion of the tertiary halogenated hydrocarbon impurity to a corresponding unhalogenated or less-halogenated unsaturated hydrocarbon and hydrogen halide, thereby providing a modified mixture;
    distilling the modified mixture to separate and recover a purified target hydrocarbon compound; and
    passing a stripping gas stream through the reaction zone.

2. The method in accordance with claim 1 wherein the tertiary halogenated hydrocarbon has a boiling point within 5° C. of the boiling point of the target hydrocarbon compound.

3. The method in accordance with claim 1 wherein the target hydrocarbon compound comprises a halogenated hydrocarbon compound.

4. The method in accordance with claim 1:
    wherein said feeding comprises feeding a flow stream comprising a liquid mixture including the tertiary halogenated hydrocarbon impurity through the reaction zone at a rate of from 0 to about 4000 weight hourly space velocity (WHSV) or feeding a flow stream comprising a gaseous mixture including the tertiary halogenated hydrocarbon impurity through the reaction zone at a rate of from 0 to about 4000 hr−1 gas hourly space velocity (GHSV);
    wherein said contacting comprises contacting the mixture containing the tertiary halogenated hydrocarbon impurity with the dehydrohalogenation catalyst at a temperature of from about 20 to about 200° C. and at a pressure of from about 0.5 to about 50 psia; and
    wherein said passing comprises passing the stripping gas stream through the reaction zone at a rate of from 0 to about 4000 hr−1 gas hourly space velocity (GHSV).

5. The method in accordance with claim 1 wherein the dehydrohalogenation catalyst comprises a sorbent-type dehydrohalogenation catalyst selected from the group consisting of activated alumina, sintered alumina, activated clay, fumed silica, silica gel, magnesium silicate, $TiO_2$, $Al_2O_3$, $ZrO_2$, $AlPO_4$ and $Al_xSi_yO_z$.

6. The method in accordance with claim 5 wherein the dehydrohalogenation catalyst is doped with a metal.

7. The method in accordance with claim 1 wherein the conversion is conducted at a temperature of from about 20 to about 150° C.

8. The method in accordance with claim 1 wherein the conversion is conducted at a pressure of from about 0.5 to about 50 psia.

9. A method for removing a tertiary halogenated hydrocarbon impurity from a target hydrocarbon compound, comprising:
- providing a first mixture comprising a target hydrocarbon compound and a tertiary halogenated hydrocarbon impurity;
- contacting the first mixture containing the tertiary halogenated hydrocarbon impurity with a dehydrohalogenation catalyst effective to catalyze a conversion of the tertiary halogenated hydrocarbon impurity to a corresponding unhalogenated or less-halogenated unsaturated hydrocarbon and hydrogen halide, thereby providing a modified mixture; and
- distilling the modified mixture to separate and recover a purified target hydrocarbon compound;
- wherein the target hydrocarbon compound comprises a chlorinated propene.

10. A method for removing a tertiary halogenated hydrocarbon impurity from a target hydrocarbon compound, comprising:
- providing a first mixture comprising a target hydrocarbon compound and a tertiary halogenated hydrocarbon impurity;
- contacting the first mixture containing the tertiary halogenated hydrocarbon impurity with a dehydrohalogenation catalyst effective to catalyze a conversion of the tertiary halogenated hydrocarbon impurity to a corresponding unhalogenated or less-halogenated unsaturated hydrocarbon and hydrogen halide, thereby providing a modified mixture; and
- distilling the modified mixture to separate and recover a purified target hydrocarbon compound;
- wherein the tertiary halogenated hydrocarbon impurity comprises a tertiary halogenated alkane or alkene having a beta hydrogen.

11. A method for removing a tertiary halogenated hydrocarbon impurity from a target hydrocarbon compound, comprising:
- providing a first mixture comprising a target hydrocarbon compound and a tertiary halogenated hydrocarbon impurity;
- contacting the first mixture containing the tertiary halogenated hydrocarbon impurity with a dehydrohalogenation catalyst effective to catalyze a conversion of the tertiary halogenated hydrocarbon impurity to a corresponding unhalogenated or less-halogenated unsaturated hydrocarbon and hydrogen halide, thereby providing a modified mixture; and
- distilling the modified mixture to separate and recover a purified target hydrocarbon compound;
- wherein the tertiary halogenated hydrocarbon impurity comprises a member selected from the group consisting of 2-chloro-2-methylepentane, 2-chloro-2,3-dimethylbutane and 4-chloro-4-methyl-1-pentene.

* * * * *